US00PP11257P

United States Patent [19]

O'Brien

[11] Patent Number: Plant 11,257

[45] Date of Patent: Feb. 29, 2000

[54] CLIMBING MINIATURE ROSE PLANT NAMED 'SAVACLEND'

[75] Inventor: Susan M. O'Brien, Chula Vista, Calif.

[73] Assignee: Nor'East Miniature Roses, Inc., Rowley, Mass.

[21] Appl. No.: 08/998,176

[22] Filed: Dec. 24, 1997

[51] Int. Cl.[7] ..... A01H 5/00

[52] U.S. Cl. ..... Plt./109

[58] Field of Search ..... Plt./109, 111, 116, Plt./123

*Primary Examiner*—Howard J. Locker

*Attorney, Agent, or Firm*—Christie, Parker & Hale, LLP

[57] ABSTRACT

A new climbing miniature rose plant variety with many petalled yellow and red blend flowers.

1 Drawing Sheet

BACKGROUND OF THE INVENTION

The present invention relates to a new and distinct variety of rose plant of the miniature rose class, which was discovered as a climbing mutation of the variety 'Savalife', U.S. Plant Pat. No. 5,482. The disclosure of U.S. Plant Pat. No. 5,482 is expressly incorporated herein by reference. The characteristics of the new variety are the same as 'Savalife' except as otherwise noted herein. The varietal denomination of this new rose is 'Savaclend'.

SUMMARY OF THE INVENTION

Among the novel characteristics possesed by this new variety which distinguishes it from its parent is its climbing rose habit.

Asexual reproduction by propagation of vegetative cuttings of the new variety as performed in Essex County, Massachusetts shows that the foregoing and other distinguishing characteristics come true to form and are established and transmitted through succeeding propagations.

COMPARISON WITH PARENT

The plant differs from 'Savalife' in that it has climbing characteristics, has a larger quantity of thorns and the stem aspect is undulate instead of straight. 'Savaclend' is further characterized by a plant that once established has a very vigorous growth habit, is easy propagate from cuttings, and has dark green foliage.

BRIEF DESCRIPTION OF ILLUSTRATION

The accompanying illustration shows typical specimens of the flowers of the new variety depicted in color as nearly true as it is reasonably possible to make the same in a color illustration of this character.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart. Phenotypic expression may vary with light availability, environmental and cultural conditions.

Parentage:

*Seed parent.*—Climbing mutation of 'Savalife'.

Class: Miniature.

The following observations are made of the specimens grown under plastic in Essex County, Mass., during August.

FLOWER

Blooming habit: Recurrent.

A. Bud:

(1) *Size.*—Medium.

(2) *Form.*—Obtuse with acute tip (3) *Color.*—When sepals first divide near 16B flushed lightly with near 39A; when petals begin to unfurl near 13A and petal tips flushed lightly with near 39A.

(4) *Sepals.*—Longer than bud, slightly foliated; near 146B; permanent; sepals usually fold back with and staying close to the petals, remaining attached after petals drop; folding back up as hip matures and dropping before hip ripens.

(5) *Peduncle.*—Length — about ¾ inches. Aspect — undulate. Strength — erect. Color — near 148C.

B. Bloom:

(1) *Size.*—Average size when fully expanded about 1¾ inches.

(2) *Borne.*—Mostly singly; sometimes in clusters.

(3) *Form.*—High centered at first; becoming flat; petals remaining at first loosely rolled outward; becoming ruffled at maturity.

(4) *Petalage.*—Number of petals under normal conditions about 30 to 36.

(5) *Color.*—Inner petals at center of flower: near 13A; reverse near 15A; outer petals near 13A with tips flushed with near 39A and near 34A; reverse near 15B with all tips flushed with near 39A and near 39B; when half-blown inner petals inside near 13B; reverse between 13A and 14A; outer petals inside between 13B and 12A and flushed from outer edges down with near 47B and 47C; reverse near 12B and flushed from tips down with near 47C and 47D; base of petals at point of attachment near 13A; general tonality from a distance red and yellow bicolor.

(6) *Color change.*—As bloom ages looking at the bloom from the top where only insides of petals show near 16B with near 39A, to near 13A with near 39A and 34A, to near 13A with near 47A and near 47B, to near 13B and 12A with 47B and 47C; and just before petal drop to near 8D and near 14C towards center with near 53B and 53D lightly flushing the entire surface; general tonality lemon yellow with outer petals lightly edged with red; after 3 or more days slightly lighter yellow and more flushed with red.

C. Petals:
(1) *Texture.*—Thick.
(2) *Appearance.*—Outside matter, inside velvety.
(3) *Form.*—Wide, oval to fan shaped.
(4) *Arrangement.*—Regularly arranged, shingle like.
(5) *Petaloids in center.*—About 2 to 15.
(6) *Persistence.*—Drop off cleanly.
(7) *Fragrance.*—None.
(8) *Lasting quality.*—About 5 to 8 days on the plant; about 6 to 9 days as a cut flower.

REPRODUCTIVE ORGANS

A. Stamens, Filaments and Anthers:
*Arrangement.*—Regularly arranged around styles.
B. Stamens:
*Quantity.*—Many.
C. Filaments:
*Approximate length.*—Uneven length, up to about 3/16 inches.
*General color.*—Between 13B and 14B.
D. Anthers:
*Color.*—Near 11C.
E. Pollen:
*Color.*—Near 22A.
*Quantity.*—Ample.
F. Pistils:
*Quantity.*—Many.
G. Styles:
*Color.*—Near 145C.
H. Stigmas:
*Color.*—Near 160D.
I. Hips: Globular, up to about 7/8 inches, near 169A, seeds do not protrude.

PLANT

A. Form: Upright, spreading.
B. Growth: Very vigorous, well branched, becoming bushy to 3 feet or more.
*Height.*—About 10 to 12 feet when mature.
*Length of flowering stem.*—Varying in length up to about 6 inches when borne singly.
C. Foliage: Compound of 5 to 7 leaflets, occasionally 3.
*Size.*—Medium.
*Quantity.*—Abundant.
*Color.*—New Foliage: Upper side near 146A; under side near 146C. Old Foliage: Upper side near 133A; under side near 191A.
*Shape.*—Oval, pointed.
*Texture.*—Upper side semi glossy; underside matte.
*Thorns or prickles.*—Many on main leaf stem.
*Edge.*—Serrated.
*Serration.*—Uneven.
*Leaf stem.*—Near 138A, underside near 144A.
*Stipules.*—Bearded with edges rolling under from the center along the length and outward as the plant ages; about 1/4 to 1/5 the length of the entire leaf.
*Resistance to diseases.*—Blackspot — Good. Mildew — Good. Rust — Good.
D. Wood:
*New wood.*—Near 60B, smooth.
*Old wood.*—Near 137C, smooth.
E. Thorns:
*Quantity.*—Ordinary.
*Form.*—Flat base tapering to long thin point, angled slightly downward.
*Length.*—Medium.
*Color.*—Near 60B.
*Position.*—Irregular.
F. Prickles:
*Main stalk.*—None.
*Laterals.*—None.
*Leaves.*—Underside of main leaf stem.
G. Winter hardiness: Needs protection in severe climates.

I claim:

1. A new and distinct climbing miniature rose plant of the variety substantially as shown and described.

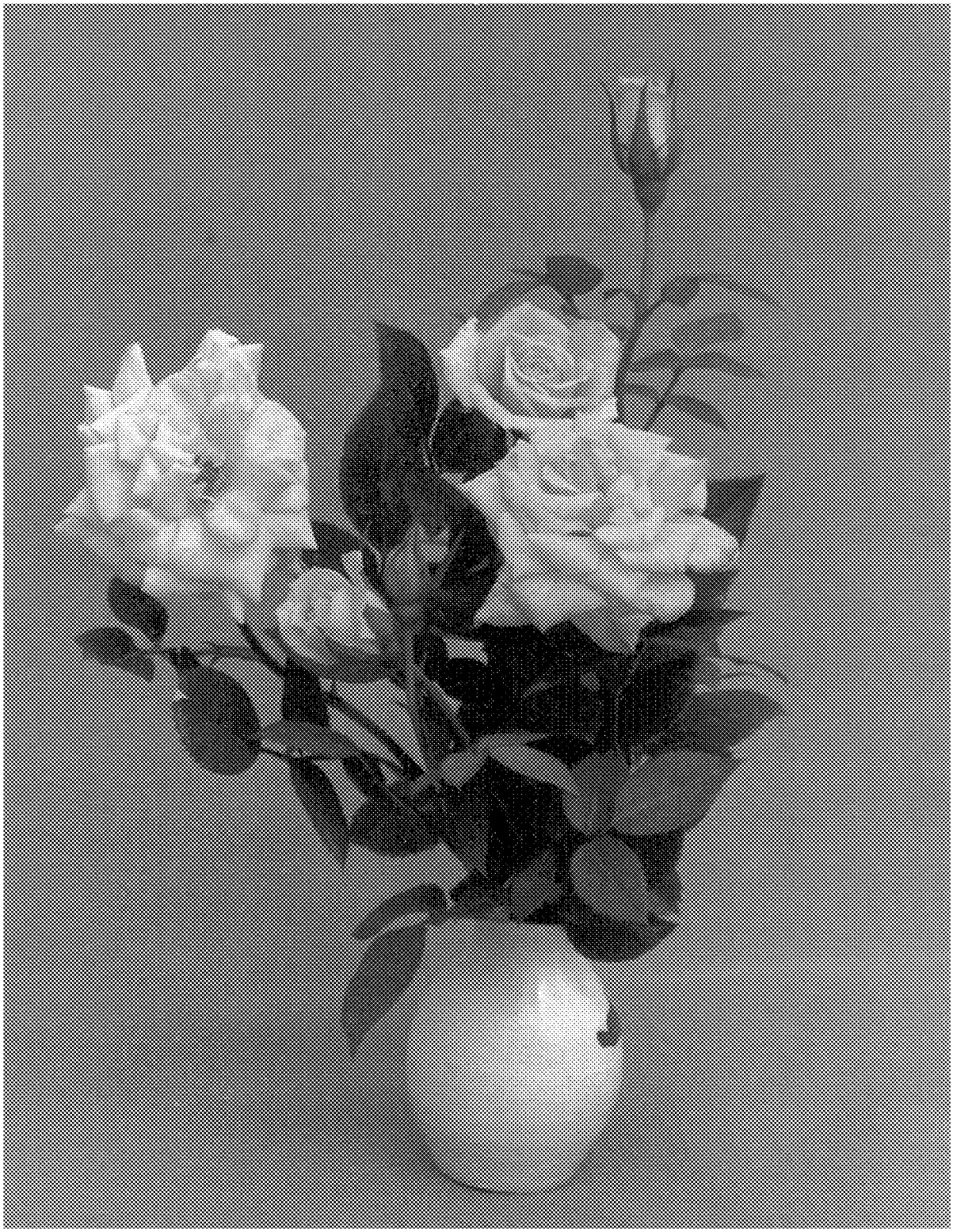

* * * * *